United States Patent [19]

Hori

[11] Patent Number: 5,183,665
[45] Date of Patent: Feb. 2, 1993

[54] COMPOSITION FOR PERCUTANEOUS ADMINISTRATION AND METHOD FOR ENHANCING PERCUTANEOUS ABSORPTION OF A PHYSIOLOGICALLY ACTIVE INGREDIENT EMPOLYING THE SAME

[75] Inventor: Mitsuhiko Hori, San Francisco, Calif.

[73] Assignee: Nitto Denko Corporation, Osaka, Japan

[21] Appl. No.: 299,506

[22] Filed: Jan. 23, 1989

[51] Int. Cl.5 .............................................. A61F 13/00
[52] U.S. Cl. .................................. 424/449; 424/447; 424/448; 514/946
[58] Field of Search ........................... 514/946, 947, ; 424/946, 947, 449

[56] References Cited

U.S. PATENT DOCUMENTS

| | | | |
|---|---|---|---|
| 4,522,826 | 6/1985 | Sunshine et al. | 514/569 |
| 4,585,783 | 4/1986 | Sunshine et al. | 514/408 |
| 4,590,190 | 5/1986 | Saito et al. | 514/221 |
| 4,654,209 | 3/1987 | Leslie et al. | 514/152 |
| 4,683,243 | 7/1987 | Sunshine et al. | 514/557 |
| 4,710,497 | 12/1987 | Heller et al. | 514/221 |
| 4,719,226 | 1/1988 | Otsuka et al. | 514/449 |
| 4,752,612 | 6/1988 | Saito et al. | 514/420 |
| 4,765,974 | 8/1988 | Tokuda et al. | 424/443 |
| 4,847,260 | 7/1989 | Abe et al. | 514/279 |

Primary Examiner—Thurman K. Page
Assistant Examiner—Leon R. Horne
Attorney, Agent, or Firm—Sughrue, Mion, Zinn, Macpeak & Seas

[57] ABSTRACT

The present invention relates to a composition for percutaneous administration which can enhance percutaneous absorption of a physiologically active ingredient and a method of enhancing percutaneous absorption of a physiologically active ingredient employing the same.

5 Claims, 2 Drawing Sheets

COMPOSITION FOR PERCUTANEOUS ADMINISTRATION AND METHOD FOR ENHANCING PERCUTANEOUS ABSORPTION OF A PHYSIOLOGICALLY ACTIVE INGREDIENT EMPOLYING THE SAME

FIELD OF THE INVENTION

The present invention relates to a composition for percutaneous administration which can enhance percutaneous absorption of a physiologically active ingredient and a method of enhancing percutaneous absorption of a physiologically active ingredient employing the same.

BACKGROUND OF THE INVENTION

Percutaneous administration of physiologically active ingredients has been carried out in order to produce topical effects on the skin or subcutaneous tissues beneath the skin. Examples of such topical effects include sterilization, disinfection, analgesia, anti-pruritus, anti-inflammation and the like.

On the other hand, oral or intravenous administration of physiologically active ingredients has been carried out in order to produce systemic effects in the subject.

Oral administration is disadvantageous in that the physiologically active ingredients so administered are susceptible to first-order metabolism in the liver. Further, in order to obtain a long-lasting effect, the concentration of the physiologically active ingredients must be initially higher than is normally necessary for effectiveness. In addition, oral administration of some physiologically active ingredients, like indomethacin, causes gastrointestinal side effects.

Intravenous administration, although advantageous for obtaining rapid absorption of the physiologically active ingredients disadvantageously requires a specialist, such as a physician.

Recently, methods for achieving systemic effects in a subject through percutaneous administration of physiologically active ingredients have been proposed in order to overcome the above-described problems associated with oral and intravenous administration of physiologically active ingredients. Percutaneous administration of physiologically active ingredients has the following advantages:

(1) the physiologically active ingredients enter from the skin directly into the blood stream and are not, therefore, susceptible to first-order metabolism in the liver, (2) the release of the physiologically active ingredients can be easily sustained, and (3) the concentration of the physiologically active ingredients in the subject is controllable.

However, the stratum corneum has long been considered a major barrier to the penetration of physiologically active ingredients (Marzulli, A. N., *J. Invest. Dermatol.*, 39:387-393 (1963)). Studies have shown that most physiologically active ingredients have a low permeability through skin. As a result, transdermal drug delivery systems have been utilized to accelerate the permeability of physiologically active ingredients through skin (Gummer, C. L., *Percutaneous Absorption*, Eds. Bronaugh, R. L. et al, Mercel Dekker Inc., New York, pages 561-570 (1985)).

Percutaneous delivery enhancers may offer a means of increasing penetration of physiologically active ingredients. For example, organic solvents such as ethanol, propylene glycol, pyrrolidones, dimethyl sulfoxide, dimethylacetamide, dimethylformamide, alkyl sulfoxide, phosphine oxide, sugar esters and surfactants are well known percutaneous delivery enhancers (Barry, B. W., *Dermatological Formulations*, Marcel Dekker Inc., New York, pages 160-172 (1983)). One enhancer, 1-dodecylazacycloheptan-2-one (Azone), has been shown to increase the absorption of antibacterial agents, antifungal agents, steroids, iododeoxyuridine and 5-fluorouracil (Stoughton, R. B., *Arch. Dermatol.*, 118:474-477 (1982); Stoughton, R. B. et al, *Drug Dev. Ind. Pharm.*, 9:725-744 (1983); Chow, D. S-L. et al, *J. Pharm. Sci.*, 73:1794-1799 (1984); Wotton, P. K. et al, *Int. J. Pharm.*, 24:19-26 (1985); Barry, B. W., *J. Contr. Rel.*, 6:85-97 (1987); and Barry, B. W. et al, *J. Pharm. Pharmacol.*, 39:535-546 (1987)). To date, the mechanism of Azone's action is not well understood. However, it is believed that the site of action is the stratum corneum (Sugibayashi, K. et al, *J. Pharm. Sci.*, 37:578-580 (1985)). Azone is minimally absorbed and that which is absorbed is removed rapidly from circulation (Wiechers, J. W. et al, *Pharm. Res.*, 4:519-523 (1987)).

In addition, is has been reported that the transport of salicylic acid and acyclovir through skin can be increased by the addition of small amounts of fatty acids or alcohols (Cooper, E. R., *J. Pharm. Sci.*, 73:1153-1156 (1984); and Cooper, E. R. et al, *J. Pharm. Sci.*, 74:688-689 (1985)).

The enhancing effect of N-decylmethyl sulfoxide on skin permeation of 5-fluorouracil has also been reported (Touitou, E. et al, *Int. J. Pharm.*, 27:89-98 (1985)).

Moreover, the enhancing effects of several amides of cyclic amines through hairless mouse skin have been reported (Mirejovsky, D. et al, *J. Pharm. Sci.*, 75:1089-1093 (1986)). Enhancers containing an azacyclo ring and terpene chain have been found to promote mitocymin C penetration through hairless mouse and rat skin (Okamoto, H. et al, *J. Pharm. Pharmacol.*, 39:531-534 (1987)).

SUMMARY OF THE INVENTION

Accordingly, an object of the present invention is to provide a composition for percutaneous administration which can enhance percutaneous permeability and percutaneous absorbability of physiologically active ingredients.

Another object of the present invention is to provide a method for enhancing percutaneous permeability and absorption of physiologically active ingredients.

These and other objects of the present invention will be apparent from the detailed description provided hereinafter.

In one embodiment, the objects of the present invention have been met by a composition for percutaneous administration comprising:

(A) a pharmaceutically effective amount of a physiologically active ingredient, and (B) a percutaneous absorption enhancing effective amount of a member selected from the group consisting of an anti-histamine, an anti-depressant, a vasodilator, an anti-psychotic, an anesthetic and an analgesic, wherein component (A) is a different compound from component (B).

In a second embodiment, the above-described objects have been met by a method for enhancing percutaneous permeability and absorption of a physiologically active ingredient comprising percutaneously administering:

(A) a pharmaceutically effective amount of a physiologically active ingredient, and (B) a percutaneous absorption enhancing effective amount of a member selected from the group consisting of an anti-histamine, an anti-depressant, a vasodilator, an anti-psychotic, an anesthetic and an analgesic, wherein component (A) is a different compound from component (B).

DETAILED DESCRIPTION OF THE INVENTION

Figure 1:
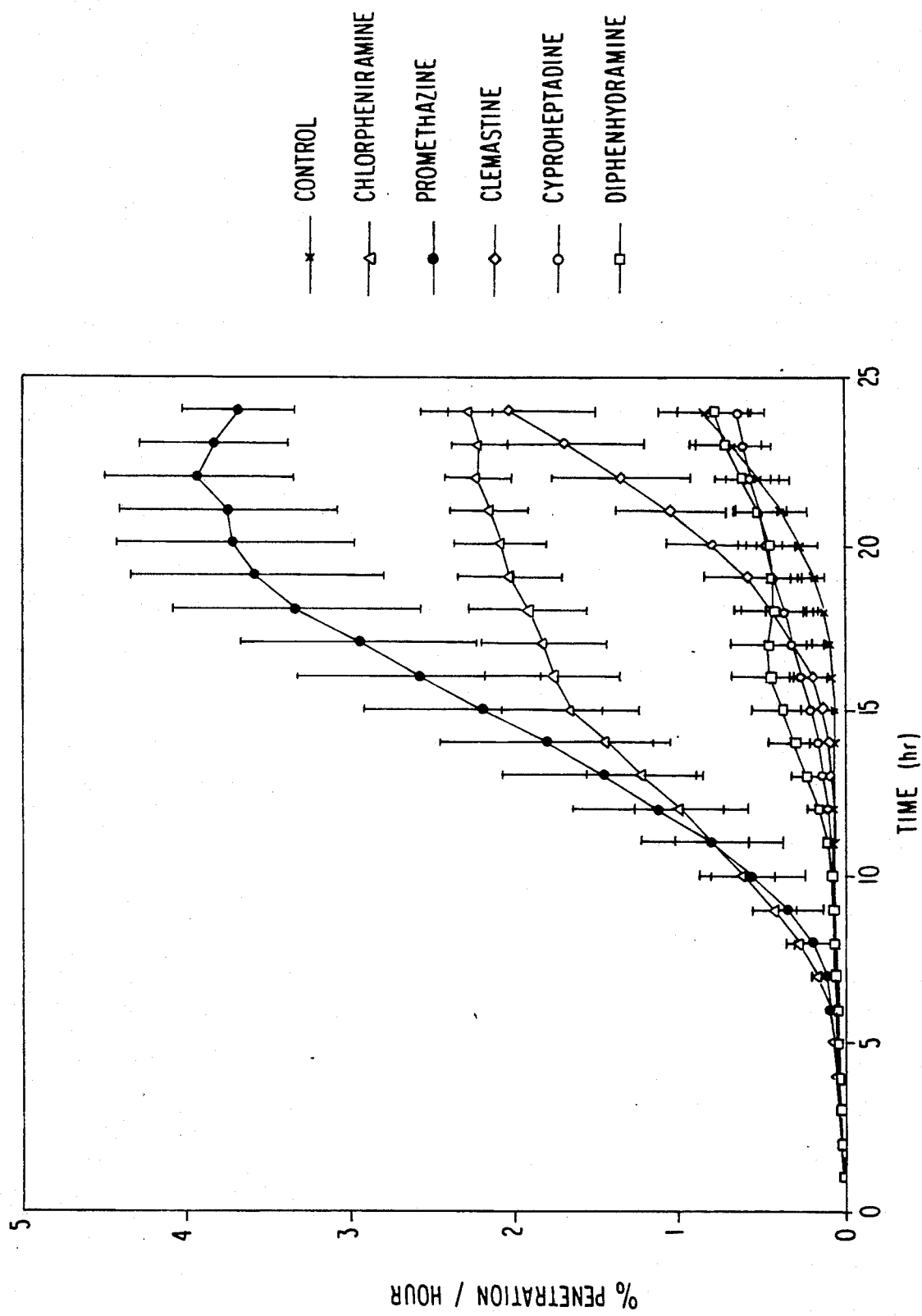
FIG. 1 illustrates the penetration percentage per hour of propranolol through hairless mouse skin with or without anti-histamines.

As discussed above, in one embodiment, the objects of the present invention have been met by a composition for percutaneous administration comprising:

(A) a pharmaceutically effective amount of a physiologically active ingredient, and (B) a percutaneous absorption enhancing effective amount of a member selected from the group consisting of an anti-histamine, an anti-depressant, a vasodilator, an anti-psychotic, an anesthetic and an analgesic, wherein component (A) is a different compound from component (B).

In contrast to cases where a physiologically active ingredient is administered for topical purposes, the composition of the present invention is useful for penetration of a physiologically active ingredient deep into the interior of the body of the subject. That is, the composition of the present invention aids in rapidly passing the physiologically active ingredient from the skin into the bloodstream.

The physiologically active ingredient to be incorporated in the composition of the present invention is not critical to the present invention. Examples of physiologically active ingredients for use in the present invention include benzodiazepins, e.g., diazepam, nitrazepam, flunitrazepam, lorazepam, prazepam, fludiazepam, clonazepam, etc.; diuretics, such as thiazides, e.g., bendroflumethiazide, polythiazide, methylclothiazide, trichlormethiazide, cyclopenthiazide, benzylhydrochlorothiazide, hydrochlorothiazide, bumetanide, etc.; hypotensives, e.g., clonidine, etc.; ethylenediamines, e.g., phenbenzamine, etc., monoamines, e.g., chlorphenylamine, etc.; non-steroid type anti-inflammatory agents, e.g., ibuprofen, ibufenac, alclofenac, diclofenac, mefenamic acid, flurbiprofen, flufenamic acid, ketoprofen, etc.; sodium salicylate, anti-cancer agents, e.g.; 5-fluorouracil, 1-(2-tetrahydrofuryl)-5-fluorouracil, cytarabine, Broxuridine, etc.; steroid type anti-inflammatory agents, e.g., cortisone, hydrocortisone, prednisolone, triamcinolone, dexamethasone, betamethasone, etc.; anti-epileptics, e.g., ethosuximide, etc.; anti-arrhythmics, e.g., ajmaline, prajmaline, pindolol, propranolol, quinidine, etc.; psychoneurotropic agents, e.g., haloperidol, moperone, etc., scopolamines, e.g., methyl scopolamine, butyl scopolamine, etc., metoclopramide hydrochloride, chloropromazine, atropines, e.g., methylatropine bromide, methylanisotropine bromide, etc.; vasodilators, e.g.; isosorbide dinitrate, nitroglycerin, pentaerythritol tetranitrate, propanyl nitrate, dipyridamole, etc.: antibiotics, such as tetracyclines, e.g., tetracycline, oxytetracycline, metacycline, doxycycline, minocycline, etc., chloramphenicols, erythromycines, and central nervous system stimulants, such as caffeine and amphetamine: and mixtures thereof.

The amount of physiologically active ingredient to be incorporated in the composition of the present invention to achieve the desired pharmaceutical effect can be readily determined depending upon the particular physiologically active ingredient employed, the body weight, the age, the sex and the symptoms of the subject. In general, the physiologically active ingredient is employed in an amount of from about 0.01 to 20% by weight, more preferably, from about 0.3 to 10% by weight, based on the total amount of the composition. However, the amount of physiologically active ingredient to be incorporated is not limited to the above-cited ranges since the amount of physiologically active ingredient to be applied can be controlled by increasing or decreasing the surface area to which the composition of the present invention is applied.

An anti-histamine is preferably employed in the present invention.

The particular anti-histamine employed in the present invention is not critical thereto as long as it is an H-1 antihistamine. Examples of anti-histamines for use in the present invention include diphenhydramine, clemastine, cyproheptadine, triperenamine, diphenylpyraline, chlorpheniramine, promethazine, doxylamine, dimenhydrimate, tripelennamine, methapyrilene, pyrilamine, thonzylamine, prophenpyridamine, chlorcyclizine, etc. and mixtures thereof. Chloropheniramine and promethazine are the preferred anti-histamines employed in the present invention.

The particular anti-depressant employed in the present invention is not critical thereto. Examples of such anti-depressants for use in present invention include amitriptyline and imipramine.

The particular vasodilator employed in the present invention is not critical thereto. Examples of such vasodilators for use in present invention include nitroglycerin, isosorbide dinitrate and prenylamine.

The particular anti-psychotic employed in the present invention is not critical thereto. Examples of such anti-psychotics for use in present invention include chlorpromazine, diazepam, haloperidol, chlordiazepoxide, medazepam, prochlorperazine and thioridazine.

The particular anesthetic employed in the present invention is not critical thereto. Examples of such anesthetics for use in present invention include cocaine, procaine, tetracaine, benzyl alcohol, chlorobutanol and ethyl aminobenzoate.

The particular analgesic employed in the present invention is not critical thereto. Examples of such analgesics for use in present invention include morphine, codeine, dextromethorphan and pethidine.

The amount of the member selected from the group consisting of an anti-histamine, an anti-depressant, a vasodilator, an anti-psychotic, an anesthetic and an analgesic to be incorporated in the composition of the present invention can be readily determined depending on the particular anti-histamine, anti-depressant, vasodilator, anti-psychotic, anesthetic and analgesic employed, the body weight, the age and sex of the subject. In general, the anti-histamine, anti-depressant, vasodilator, anti-psychotic, anesthetic and analgesic is employed in an amount of from about 0.01 to 20%, preferably 0.3 to 10% by weight based on the total weight of the composition.

The composition of the present invention is prepared by adding the physiologically active ingredient and the member selected from the group consisting of an anti-histamine, an anti-depressant, a vasodilator, an anti-psychotic, an anesthetic and an analgesic separately to an appropriate solvent and then admixing the two solutions or by adding the physiologically active ingredient and the member selected from the group consisting of an anti-histamine, an anti-depressant, a vasodilator, an anti-psychotic, an anesthetic and an analgesic together to an appropriate solvent. The particular solvent employed in the present invention is not critical thereto. Examples of such solvents include ethanol, propanol, tertiary butanol, N-methypyrrolidone and propylene glycol.

The composition of the present invention may further contain conventional pharmaceutically acceptable additives and can be formulated into various dosage forms for external use such as ointments, plasters, lotions, adhesive tapes, impregnants, gels, etc.

The impregnants are prepared by absorbing the composition of the present invention in an appropriate absorbant, such as gauze, filter paper, porous membrane, etc., and generally applied to the skin with the aid of adhesive tape.

The gels are prepared by gelling the composition of the present invention with, for example, dibenzolidene sorbitol (e.g., "Gelol D", a trademark for a product manufacture by New Japan Chemical Co., Ltd.) and spreading the jelly on a support.

Bases which can be employed for the adhesive tapes are well known in the art and include acrylic polymers, polyvinyl ether compounds, rubber adhesive mixtures and the like.

Other dosage forms for external use can be prepared by methods well known in the art.

As discussed above, in another embodiment of the present invention, the above-described objects have been met by a method for enhancing percutaneous permeability and absorption of a physiologically active ingredient comprising percutaneously administering:

(A) a pharmaceutically effective amount of a physiologically active ingredient, and (B) a percutaneous absorption enhancing effective amount of a member selected from the group consisting of an anti-histamine, an anti-depressant, a vasodilator, an anti-psychotic, an anesthetic and an analgesic, wherein component (A) is a different compound from component (B).

The member selected from the group consisting of an anti-histamine, an anti-depressant, a vasodilator, an anti-psychotic, an anesthetic and an analgesic increases percutaneous permeability and percutaneous absorbability of the physiologically active ingredient. The systemic effects achieved in the present invention can be produced by percutaneously administering the physiologically active ingredient simultaneously with the member selected from the group consisting of an anti-histamine, an anti-depressant, a vasodilator, an anti-psychotic, an anesthetic and an analgesic. It is preferred that the physiologically active ingredient is admixed with the member selected from the group consisting of an anti-histamine, an anti-depressant, a vasodilator, an anti-psychotic, an anesthetic and an analgesic prior to percutaneous administration.

The following examples are provided for illustrative purposes only and are in no way intended to limit the scope of the present invention. In these examples, all percents are by weight unless otherwise indicated.

EXAMPLE 1

The penetration enhancing effect of anti-histamines for the percutaneous administration of propranolol and diazepam through hairless mouse skin is demonstrated in this example.

Figure 2:
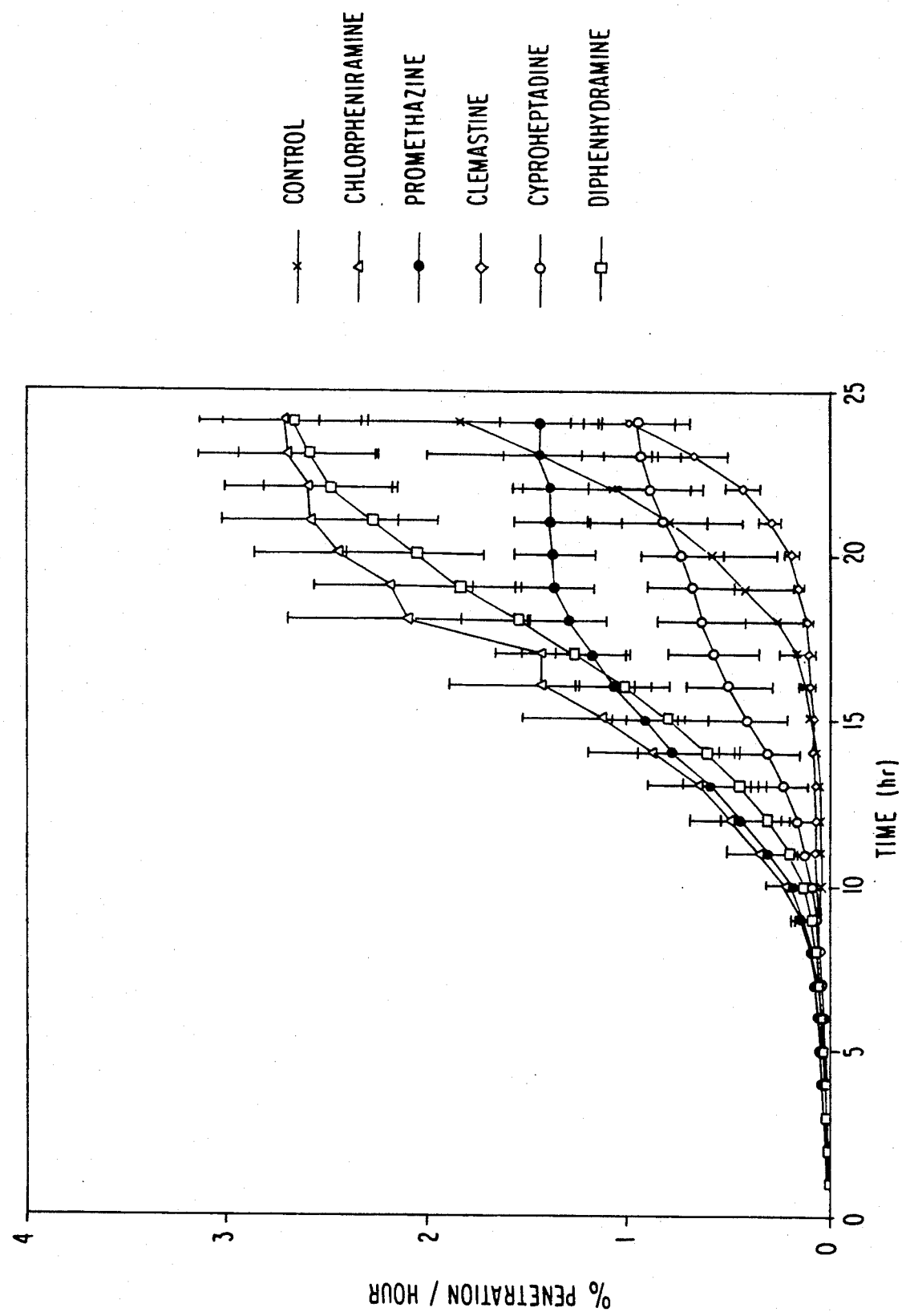
FIG. 2 illustrates the penetration percentage per hour of diazepam through hairless mouse skin with or without anti-histamines.

The whole skin of female hairless mice, killed by $CO_2$ asphyxiation, was removed. Then, superficial muscle tissue and subcutaneous fat were removed from the whole skin. The excess skin was placed on a flow-through penetration cell having a surface area of 0.785 $cm^2$ (1.0 cm in diameter). Next, a 0.5 ml ethanol solution containing 4.0% (w/v) of either chlorpheniramine, promethazine, cyproheptadine, or diphenhydramine or containing 0.5% (w/v) of clemastine, and 0.1% (w/v) of either $^3$H-propranolol or $^3$H-diazepam was applied to the surface of the mouse skin. The contents of the cells were stirred continuously and maintained at 37° C. throughout the experiment. Continuous sampling of the saline receptor phase for 24 hours was achieved using an automatic fraction collector. All of the samples were assayed for radioactivity by liquid scintillation counter. The results are shown in FIG. 1 (propranolol) and FIG. 2 (diazepam). The results are summarized in Table 1 below.

TABLE 1

| Physiologically Active Ingredient | Anti-histamine | PR* | ER** | Lag Time (hrs) |
|---|---|---|---|---|
| Diazepam | — | 7.2 | — | 15 |
| Diazepam | Chlorpheniramine | 24.1 | 3.3 | 6 |
| Diazepam | Promethazine | 15.5 | 2.2 | 7 |
| Diazepam | Cyproheptadine | 8.1 | 1.1 | 10 |
| Diazepam | Clemastine | 3.7 | 0.5 | 15 |
| Diazepam | Diphenhydramine | 20.5 | 2.8 | 9 |
| Propranolol | — | 3.7 | — | 16 |
| Propranolol | Chlorpheniramine | 26.2 | 7.1 | 6 |
| Propranolol | Promethazine | 39.9 | 10.8 | 6 |
| Propranolol | Cyproheptadine | 5.1 | 1.4 | 12 |
| Propranolol | Clemastine | 9.4 | 2.5 | 12 |
| Propranolol | Diphenhydramine | 6.3 | 1.7 | 10 |

*PR = the penetration ratio of the applied physiologically active ingredient; PR = Penetration amount/application amount × 100%.
**ER = the estimation ratio of the enhancing effect of anti-histamines; ER = PR with anti-histamines/PR without anti-histamines (control).

As shown in Table 1 above, chlorpheniramine and diphenylhydramine enhanced the penetration of diazepam 3.3 and 2.8 times, respectively, greater than the control over 24 hours and decreased the lagtime from 15 to about 6 hours. Further, chlorpheniramine and promethazine enhancing the penetration of propranolol about 7.1 and 10.8 times, respectively, greater than the control over 24 hours and decreased the lagtime from 16 to 6 hours.

EXAMPLE 2

The penetration enhancing effect of anti-histamines for the percutaneous administration of caffeine through hairless mouse skin is demonstrated in this example.

The procedures in Example 1 were repeated using a 0.1% (w/v) solution of $^{14}$C-caffeine containing the anti-histamines in the concentrations set forth in Table 2 below. The results obtained are shown in Table 2 below.

TABLE 2

| Anti-histamine | PR | ER |
|---|---|---|
| — | 17.0 | — |
| Chlorphenylamine (0.8% w/v) | 48.7 | 2.9 |
| Chlorpheniramine (4.0% w/v) | 33.0 | 1.9 |
| Promethazine (0.8% w/v) | 33.3 | 2.0 |
| Promethazine (4.0% w/v) | 43.2 | 2.5 |
| Cyproheptadine (0.8% w/v) | 31.6 | 1.9 |
| Cyproheptadine (4.0% w/v) | 24.8 | 1.5 |
| Clemastine (0.1% w/v) | 20.6 | 1.2 |
| Clemastine (0.5% w/v) | 15.2 | 0.9 |
| Diphenhydramine (4.0% w/v) | 20.9 | 1.2 |

As shown in Table 2 above, using anti-histamines, there was an up to 2.9 times greater enhancement of penetration of caffeine compared to the control.

While this invention has been described in detail and with reference to specific embodiments thereof, it will be apparent to one skilled in the art that various changes and modifications could be made therein without departing from the spirit and scope thereof.

I claim:

1. A method for enhancing percutaneous permeability and absorption of a physiologically active ingredient comprising percutaneously administering:
   (a) a pharmaceutically effective amount of a physiologically active ingredient selected from at least one member of the group consisting of a benzodiazepin, a diuretic, a hypertensive, an ethylenediamine, a non-steroid anti-inflammatory agent, sodium salicylate, an anti-cancer agent, a steroid anti-inflammatory agent, an anti-epileptic, an anti-arrhythmic, a psychoneurotropic agent, an antibiotic and a central nervous system stimulant, wherein said pharmaceutically effective amount is about 0.01 to 20% by weight of the total composition, and
   (b) a percutaneous absorption enhancing effective amount of an anti-histamine selected from the group consisting of diphehydramine, clematine, cyproheptadine, triperenamine, diphenylpyraline, chlorpheniramine, promethazine, doxylamine, dimenhydrimate, tripelennamine, methapyrilene, pyrilene, thonzylamine, prophenpyridamine and chlorcyclizine, wherein said percutaneous absorption enhancing effective amount is about 0.01 to 20% by weight of the total composition, wherein component (A) is a different compound from component (B).

2. The method as claimed in claim 1, wherein said pharmaceutically effective amount is about 0.3 to 10% by weight of the total composition.

3. The method as claimed in claim 1, wherein said percutaneous absorption enhancing effective amount is about 0.3 to 10% by weight of the total composition.

4. The method as claimed in claim 1, wherein said anti-arrhythmic is propranolol.

5. The method as claimed in claim 1, wherein said anti-arrhythmic is propranolol and said anti-histamine is promethazine.

* * * * *